(12) United States Patent
Burke

(10) Patent No.: US 8,251,964 B1
(45) Date of Patent: Aug. 28, 2012

(54) SANITARY DEVICE AND METHOD

(76) Inventor: Thomas J. Burke, Whitehouse Station, NJ (US)

( * ) Notice: Subject to any disclaimer, the term of this patent is extended or adjusted under 35 U.S.C. 154(b) by 450 days.

(21) Appl. No.: 12/456,551

(22) Filed: Jun. 18, 2009

Related U.S. Application Data

(60) Provisional application No. 61/132,500, filed on Jun. 19, 2008.

(51) Int. Cl.
*A61F 5/44* (2006.01)
(52) U.S. Cl. .................. 604/347; 604/349; 604/346
(58) Field of Classification Search .......... 604/346–349, 604/358
See application file for complete search history.

(56) References Cited

U.S. PATENT DOCUMENTS 6,105,174 A * 8/2000 Nygren et al. .................... 2/403
6,129,719 A * 10/2000 Nozaki et al. ............ 604/385.01

* cited by examiner

*Primary Examiner* — Michele M Kidwell
(74) *Attorney, Agent, or Firm* — Joanne M. Martin

(57) ABSTRACT

The present invention provides a sanitary device having a significant capacity (e.g. 30 c.c.) in an plastic pouch (or envelope) gently attached to the end of the male member by releasable pressure sensitive adhesive across an opening which receives the male member. The pressure sensitive adhesive provides close connection to the skin, provides a fluid closure around the male member, and permits closure with opposing adhesive surfaces of the sanitary device not used to surround the circumference of the inserted male member. A further feature provides flaps, tabs or margins at the sanitary device opening which are foldable over the adhesive to selectably cover some portion or all of the adhesive as may be desired by the wearer.

9 Claims, 1 Drawing Sheet

SANITARY DEVICE AND METHOD

The present invention incorporates by reference co-pending patent application Ser. No. 11/903,997, filed Sep. 25, 2007, entitled SANITARY DEVICE, and claims priority on and incorporates by reference previously filed copending provisional patent application Ser. No. 61/132,500 filed Jun. 19, 2008.

FIELD OF THE INVENTION

The present invention relates to sanitary devices, in particular to sanitary devices for absorbing limited male incontinence.

BACKGROUND OF THE INVENTION

The nature of the male member through which limited incontinence, e.g. "dripping" issue, its location typically under multiple layers of garments and the activity and motion of the user can make effective sanitary noticeably uncomfortable. Alternately, more comfortable sanitary devices can be less effective, expensive or hard to use.

SUMMARY OF THE INVENTION

The present invention provides a sanitary device having a significant capacity (e.g. 30 c.c.) in an plastic pouch (or envelope) gently attached to the end of the male member by releasable pressure sensitive adhesive across an opening which receives the male member. The pressure sensitive adhesive provides close connection to the skin on the surface of the male member which is typically movable relative to generally flaccid to semi-rigid tissue, thus providing a secure attachment to male member as the wearer moves and causes movement thereof, and provides a fluid closure around the male member, and permits closure with opposing adhesive surfaces of the sanitary device not used to surround the circumference of the inserted male member.

A further feature provides flaps, tabs or margins at the sanitary device opening which are foldable over the adhesive to selectably cover some portion or all of the adhesive as may be desired by the wearer.

BRIEF DESCRIPTION OF THE DRAWING

These and further features of the present invention will be better understood by reading the following Detailed Description together with the Drawing, wherein.

DETAILED DESCRIPTION OF THE EXEMPLARY EMBODIMENT

Figure 1:
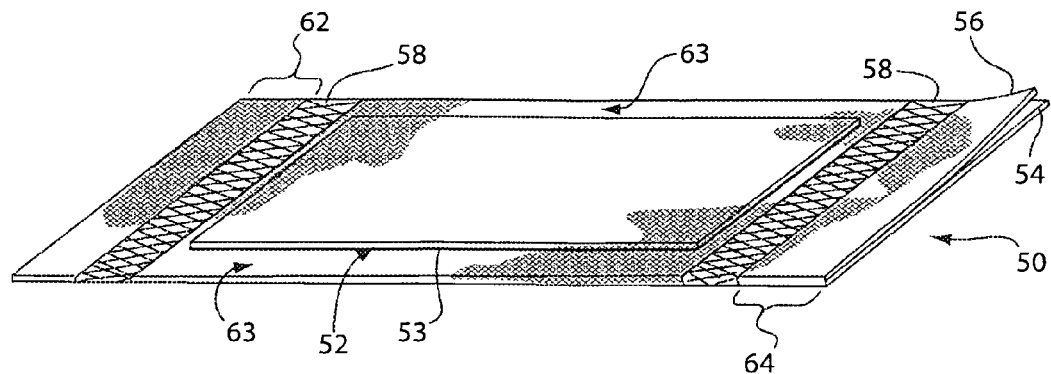
FIG. 1 is a perspective drawing of a partially assembled sanitary device according to an exemplary embodiment of the present invention.

An early stage of the assembly process to provide the embodiment 50 of FIG. 1 shows an absorbent pad 52, comprising suitable materials such as Unipro 50WW manufactured by Midwest Filtration Company, retained on a plastic (or other waterproof) layer 54 and covered by a non-woven material 56 sized and located to provide margins 62, 63, 64 therearound. The non-woven material is chosen to provide fluid movement therethrough into the absorbent pad, and if possible, to discourage fluid flow out of the absorbent pad 52. The absorbent pad 52 may also include a backing material 53 which is interposed between the pad 52 absorbent material and the layer 54. A material such as product B0006 manufactured by PGI Nonwovens, can be used as the non-woven material 56. Strips 58 of pressure sensitive adhesive, such as H3513 Pressure Sensitive adhesive manufactured by Heartland Adhesives & Coatings, Inc. of Germantown, Wis., or equivalent or similar, are applied on the opposite margins of the overlaying layers 54 and 56, and in the exemplary embodiment 50 of FIG. 1 leaving margins 62 and 64 without adhesive thereon. The preferred adhesive aggressive enough to secure to the wearer's skin while being mild enough to avoid unacceptable chafing or irritation. Also, the adhesive strip 58 is sufficiently aggressive to provide the desired fluid barrier, yet mild enough to permit separation to permit insertion of the male member therebetween. In the embodiment 50, the smaller dimension of margin 62 is less than the smaller dimension of margin 64.

Figure 2:
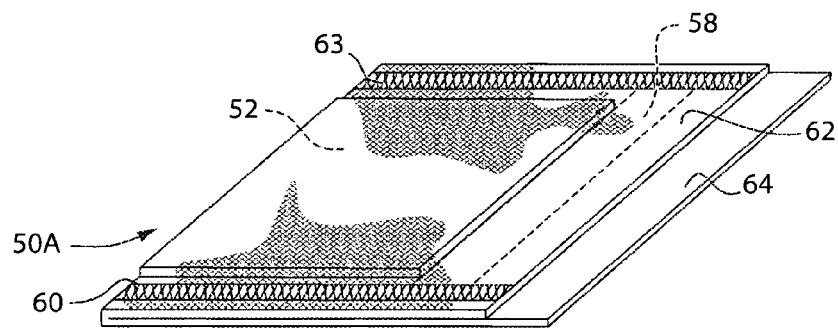
FIG. 2 is a perspective drawing of the embodiment of FIG. 1 folded and edge-sealed to form a pocket.

The embodiment 50 is folded to provide the embodiment 50A shown in FIG. 2, wherein the adhesive layers 58 at least partially overlap and engage. The margins 63 overlap themselves when the structure 50 is folded and are held closed by a fluid-tight weld 60, adhesive, etc. to form a fluid pouch which together with the absorbent pad 52 can retain a volume of fluid, e.g. 30 cc, typically from the limited incontinence of the wearer.

Figure 3:
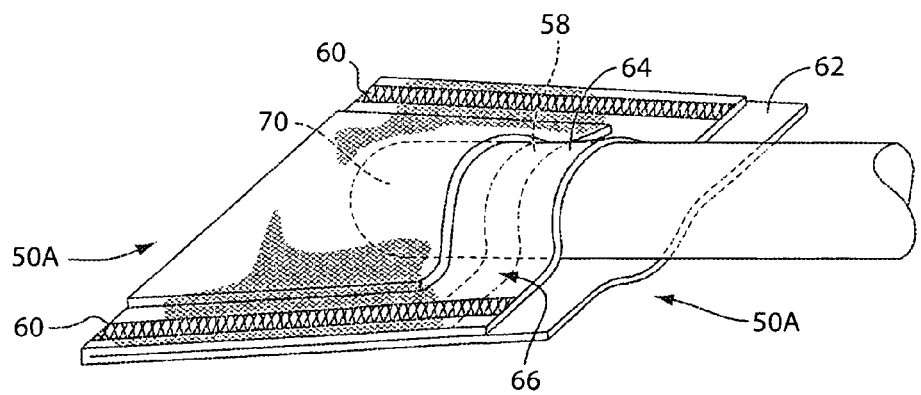
FIG. 3 is a perspective drawing of the embodiment of FIG. 2, showing deformation and sealing about an included representation of the male member inserted into the embodiment of the sanitary device.

Should the user wish to avoid attachment with the adhesive, one or both margins 62, 64 may be folded over the adhesive strip 58 of all or a part thereof. Application of the embodiment 50A to a male member 70 is shown in FIG. 3, wherein after the male member is inserted into the interior volume formed by the welded (60) layer 54, the substantially facing adhesive layers 58 are urged onto the outerlaying skin surface of the male member 70. Any portion, e.g. 66, of the opening not surrounding (contacting) the male member is closed to fluid flow by re-engaging the corresponding portion of the adhesive strip 58. In subsequent use, any fluid from user 'dripping' is absorbed through the material 56 into the absorbent pad 52 and retained therein. For removal, the margins of device 50A are released from the male member by separating the adhesive layers 58 from the male member, and the device 50 simply slides off. The adhesive layers may be joined to seal the device and retain fluid therein for convenient disposal.

Modifications and substitutions made by one of ordinary skill in the art are within the scope of the present invention, which is not limited except by the claims as subsequently added.

What is claimed is:

1. An absorbent device, comprising:
a pliant, substantially waterproof planar member having an area and an edge thereabout;
an absorbent pad disposed on said planar member having a margin thereabout on said planar member;
a fluid-permeable layer disposed over said absorbent pad and retained to said planar member at said margin; and
an adhesive disposed in a portion of said margin and spaced from said edge by a selected dimension to form a flap from said planar member between said edge and said adhesive, wherein
said planar member together with said absorbent pad and said fluid permeable layer, are folded at a fold and bonded with a bond on confronting portions of said margin extending away from said from fold to define a volume therebetween including said absorbent pad having an opening into said volume including said adhesive at least partially thereacross, and wherein said flap is selectively foldable to at least partially cover said adhesive.

2. The absorbent device of claim 1, wherein said adhesive comprises adhesive disposed on confronting portions of said folded planar member.

3. The absorbent device of claim 2, wherein each said confronting portions having adhesive thereon further includes a flap comprising a portion of said planar member extending beyond said adhesive.

4. The absorbent device of claim 3, wherein said adhesive on confronting portions at least partially overlap.

5. The absorbent device of claim 3, wherein said adhesive comprises an adhesive which permits separation when in contact with each other while providing secure attachment to a member inserted therebetween.

6. The absorbent device of claim 1, wherein said bond comprises one of a weld and an adhesive bond.

7. The absorbent device of claim 1, wherein said planar member comprises a plastic material.

8. The absorbent device of claim 1, wherein said volume comprises a substantially fluid-tight volume.

9. The absorbent device of claim 1, wherein said fluid-permeable layer comprises non-woven material.

* * * * *